United States Patent [19]

Fagan, Jr. et al.

[11] 4,050,157
[45] Sept. 27, 1977

[54] DENTAL IMPLANT

[76] Inventors: Maurice J. Fagan, Jr.; Maurice J. Fagan, III, both of 5360 Peachtree Dunwoody Road NE., Atlanta, Ga. 30342

[21] Appl. No.: 581,419

[22] Filed: May 27, 1975

[51] Int. Cl.² .......................................... A61C 13/00
[52] U.S. Cl. .................................................. 32/10 A
[58] Field of Search ...................... 32/10 A; 128/92 C

[56] References Cited

U.S. PATENT DOCUMENTS

| | | | |
|---|---|---|---|
| 3,729,825 | 5/1973 | Linkow et al. | 32/10 A |
| 3,798,771 | 3/1974 | Edelman | 32/10 A |
| 3,829,972 | 8/1974 | Pasqualini et al. | 32/10 A |
| 3,849,888 | 11/1974 | Linkow | 32/10 A |
| 3,977,081 | 8/1976 | Zambelli | 32/10 A |

FOREIGN PATENT DOCUMENTS

| | | | |
|---|---|---|---|
| 2,522,433 | 11/1975 | Germany | 32/10 A |
| 1,278,966 | 6/1972 | United Kingdom | 32/10 A |
| 1,278,967 | 6/1972 | United Kingdom | 32/10 A |

Primary Examiner—Robert Peshock
Attorney, Agent, or Firm—Clarence A. O'Brien; Harvey B. Jacobson

[57] ABSTRACT

A dental implant for anchoring attachments to the jawbone including a flat base embedded entirely within the bone tissue of the mandibular or maxillary ridge. A support head is connected to the base by a shank having a necked down portion spaced from the base and confined to the gingival. A stabilizer formation spaced lingually from the base in overlying relation to a rectangular opening formed therein, is connected to the edge portion of the base from which the shank projects.

6 Claims, 10 Drawing Figures

DENTAL IMPLANT

BACKGROUND OF THE INVENTION

This invention relates to the permanent anchoring of dental attachments to the jawbone of a patient by use of a metallic implant.

The use of implants in the bone tissue of the mandibular ridge for anchoring of dental attachments such as artificial teeth and crowns, are well known. In some prior art arrangements the implant is of an elastically resilient type occupying the socket from which the root portion of a natural tooth was extracted. Other prior art implants feature relatively thin, blade elements embedded in the bone tissue without regard to any socket remaining after extraction of the natural tooth. A major problem arising with such dental implants resides in the unfavorable reaction of bone tissue to forces transmitted through the dental implants. Occlusal forces applied either obliquely or producing a horizontal component when acting upon cuspal inclinations, cause mobility and/or injury because of the ill effects of the leverage associated with such dental implants. Very often, such prior dental implants will loosen or cause periodontal destruction to a greater extent than that occasioned with natural teeth in a weakened environment.

It is therefore an important object of the present invention to provide a dental implant for anchoring dental attachments in such a manner as to improve reaction of bone tissue to transmitted forces by a beneficial modification in the leverage arrangement of the dental implant as compared to that of the natural tooth and the leverage arrangements associated with prior dental implants.

In accordance with the present invention, a dental implant is arranged to stabilize itself once embedded within the bone tissue in order to better resist those occlusal forces tending to rotate the tooth about its center of rotation causing periodontal destruction and loosening of the implant. This is effected by a special design of the implant body which raises the center of rotation from the usual location associated with the root portion of a normal tooth and balances moments tending to produce implant rotation. As in the case of the Linkow and Edelman patents aforementioned, the implant body of the present invention includes a substantially thin, planar base or blade embedded within the bone tissue of the mandibular ridge. Unlike, the implant bodies disclosed in the foregoing prior art patents, however, the base of the dental implant according to the present invention is provided with a rounded bottom edge in order to produce a stabilizing effect on the implant base by preventing buccal-lingual movement. The other edge of the implant base is spaced from the crest of the ridge by a distance equal to a rectangular shoulder portion of a shank projecting from this edge of the base toward a support abutment exposed above the gum line and on which an attachment crown in secured. The shank projecting from the base is provided with a necked down portion confined to the gingival and terminating in an enlarged gingival collar from which the support abutment projects. A peripheral shoulder surface on the gingival collar is exposed in surrounding relation to the support abutment in order to receive the connecting crown of a fixed bridge, for example. The necked down portion of the shank provides a tight gingival attachment. The base extends laterally in a mesial-distal direction from the shank with the side surfaces thereof recessed and provided with at least one substantially rectangular opening through which bone tissue may grow after the implant body has been inserted. A stabilizer formation is connected to the edge portion of the implant base from which the shank projects and extends in substantially parallel spaced relation to the relatively planar base in overlying alignment with the rectangular opening. The edge portion of the implant base from which the shank projects is provided with a flat edge surface within which a groove and notch may be formed for an implant inserting instrument.

The stabilizer formation, the rounded bottom edge on the implant base and the recessed intermediate portions of the base along its length in the mesial-distal direction, prevents loosening of the implant once properly inserted with the proper prosthetic appliance thereon. The foregoing arrangement is such that occlusal forces applied to the dental attachment will result in an equilibrium of moments and a favorable transmission of tensile forces so that the bone is stimulated and deposited through the rectangular openings in the implant base by the adjacent trabeculated bone. The implant body is thus retained in place with a minimum of fibrous connective tissue separating the metal portion of the implant base from the trabeculated bone.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
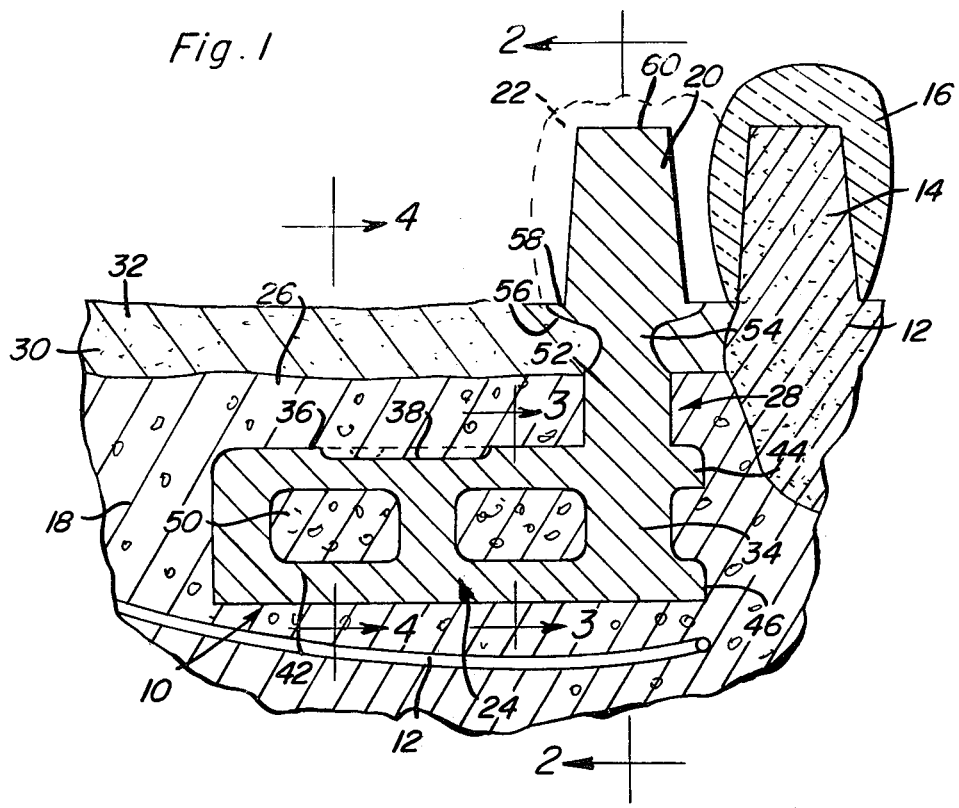
FIG. 1 is a sectional view through a portion of a lower mandible or jawbone within which a dental implant has been inserted in accordance with the present invention.
Figure 2:
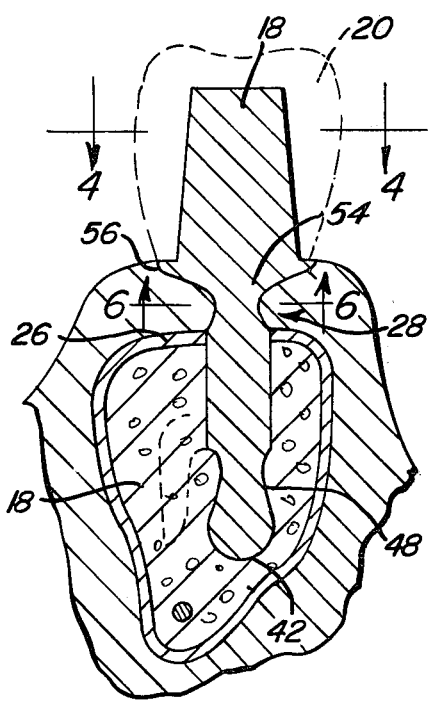
FIG. 2 is a sectional view taken substantially through a plane indicated by section line 2—2 in FIG. 1.

Referring now to the drawings in detail, FIGS. 1 and 2 illustrate a typical implantation in a lower mandible or jawbone of a patient of a dental implant body of the blade type generally referred to by reference numeral 10 adjacent to a natural tooth root 12 having a ground down projecting stub 14 on which an artificial tooth 16 is seated and secured. The implant body 10 is accordingly embedded within the bony tissue 18 of the jawbone above the nerve chanel 12. Projecting from the implant body is an abutment support 20 to which a connecting crown 22 is adapted to be secured as shown by dotted lines. The crown 22 may be made of porcelain or acrylic and form part of a fixed bridge that is permanently anchored to the jawbone by means of the implant body 10.

In the embodiment illustrated in FIGS. 1 and 2, the implant body 10 includes a substantially planar base generally referred to by reference numeral 24. The base is embedded entirely within the bone tissue 18 spaced from the ridge crest 26. The abutment support 20 is connected to the base by means of a shank generally referred to by reference numeral 28. The shank 28 thus projects from the base 24 to the ridge crest 26 and extends through the gingival 30 to the gum line 32 at which the shank is connected to the abutment support 20. The root axis 34 associated with the crown 22 extends centrally through the abutment support 20 and the shank 28 to which it is connected.

Figure 5:
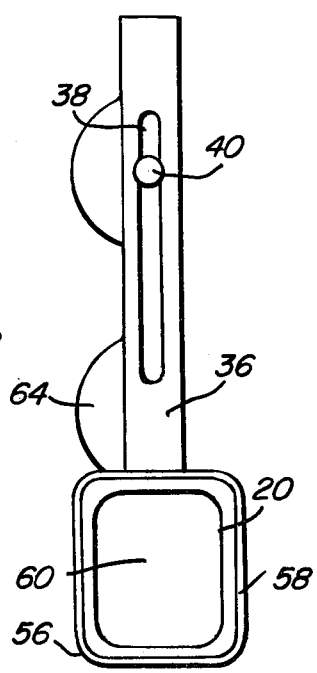
FIG. 5 is a top view of the dental implant shown in FIG. 4.

The base 24 extends transversely of the root axis from the shank in a mesial-distal direction within the bone tissue as more clearly seen in FIG. 1. The longitudinal edge portion 36 of the base from which the shank 28 extends, is formed with a flat edge surface spaced from the ridge crest 26 by a predetermined distance such as 2.5 millimeters. An elongated groove 38 as shown in FIGS. 1 and 5, is formed in the flat edge surface 36 for receiving an inserting instrument. A circular notch 40 is also formed in the edge surface 36 as shown in FIG. 5 for receiving an inserting instrument. In the illustrated embodiment, the other longitudinal edge portion 42 of the base is rounded as shown in FIG. 2. The two edge portions 36 and 42 of the base extend beyond the shank 28 and terminate in rounded formation 44 and 46. The side surfaces 48 of the base intermediate these spaced edge portions 36 and 42, are inwardly recessed and are formed with spaced, substantially rectangular openings 50 through which bone tissue is adapted to grow for anchoring of the implant body therein as more clearly seen in FIG. 3.

Figure 6:
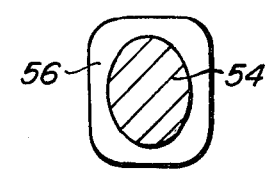
FIG. 6 is a partial sectional view taken substantially through a plane indicated by section line 6—6 in FIG. 2.

The shank 28 includes a cross-sectionally rectangular shoulder portion 52 which is a continuation of the base 24 and is therefore of the same thickness. The shoulder portion extends from the base to the ridge crest 26 and therefore determines the depth to which the base is embedded within the bone tissue from ridge crest. Extending from the shoulder portion 52 through the gingival orgum tissues 30, is a neck portion 54. The neck portion 54 is cross-sectionally smaller than the shoulder portion 52 or the abutment support 20 to which it is connected. As shown in FIG. 6, the neck portion is elliptical in cross-section. The neck portion flares radially outwardly into a gradually enlarged gingival collar 56 having a peripheral shoulder surface exposed at the gum line 32 in surrounding relation to the abutment support 20. The shoulder surface 58 which may be 0.8 millimeters wide, for example, forms an abutment surface for the connecting crown 22 as shown in FIG. 1. The neck portion 54 between the shoulder portion 52 and the gingival collar forms a tight fit within the gum tissue to which it is confined.

The abutment support 20 is of a non-planar shape as compared to the base 24 and tapers from the radially enlarged gingival collar 56 in a converging direction to a top surface 60. The sides of the abutment support are rounded as more clearly seen in FIG. 5.

Figure 3:
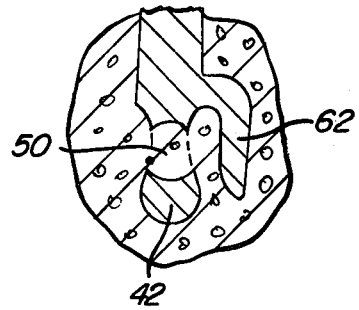
FIG. 3 is a partial sectional view taken substantially through a plane indicated by a section line 3—3 in FIG. 1.
Figure 4:
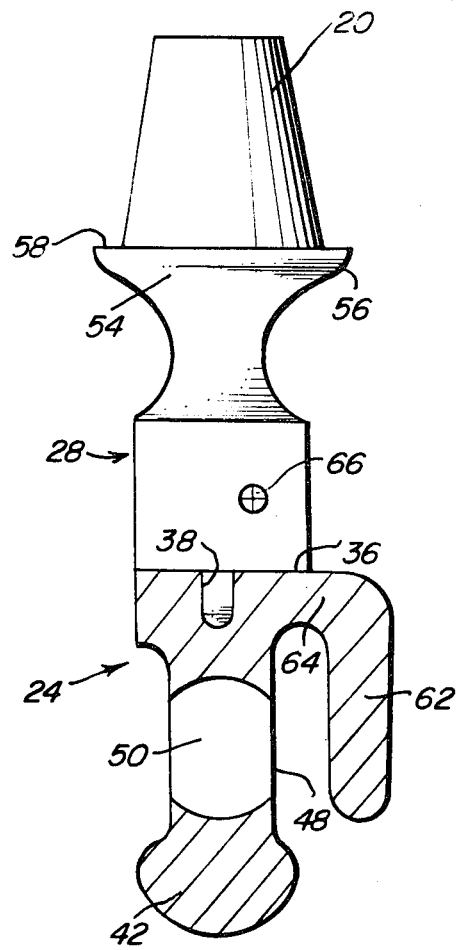
FIG. 4 is an enlarged sectional view taken substantially through a plane indicated by section line 4—4 in FIG. 1 with all of the oral tissues removed.

As more clearly seen in FIGS. 3 and 4, a stabilizer formation 62 is connected to the base in overlying relationship to each of the rectangular openings 50. Each stabilizer formation 62 is therefore connected to the edge portion 36 of the base by a connective portion 64 which extends substantially the length of its associated opening 50.

As a result of the shape and configuration of the implant body 10 hereinbefore described, the center of mass or rotation 66 as indicated in FIG. 4 assumes a position raised above that normally associated with a natural tooth or dental implants heretofore provided. The center of rotation 66 occupies a geometrical relationship to the implant body such that an equilibrium of moments is established whenever forces are transmitted by the implant body to the bone tissue as a result of occlusal forces applied to the abutment support from the crown. Accordingly, a more favorable reaction of the bone tissue is obtained to the forces transmitted as hereinbefore indicated. As shown in FIG. 4, this favorable geometric relationship results from the positioning of the center of rotation midway between the neck portion 54 of the shank and the flat edge portion 36 of the base.

Figure 7:
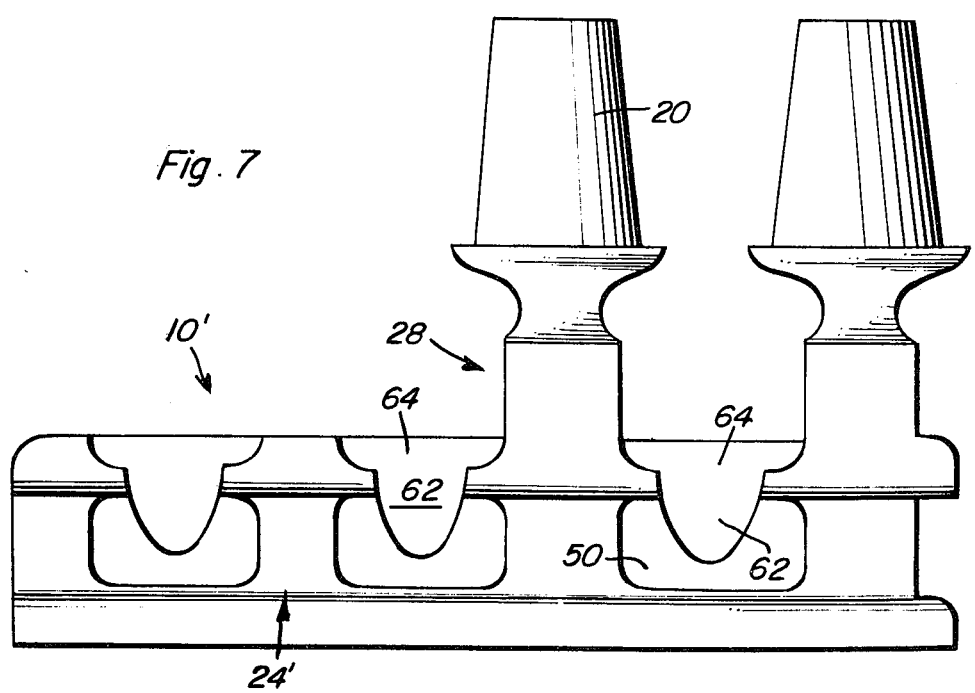
FIG. 7 is a front elevational view of another form of dental implant.

In FIG. 7, a dental implant is shown generally referred to by reference numeral 10; which embodies the same basic structural features of the dental implant 10 depicted in FIGS. 1-5. The implant body 10′, however, is provided with two shanks 28 and associated abutment supports 20 spaced from each other by a base 24′ having an additional section disposed between the two shanks 28 and provided with an addditional rectangular opening 50 and an associated stabilizer formation 62 connected to the base by connecting portion 64 which extends between the two shanks 28. The implant body 10′ will, of course, be utilized for the permanent anchoring of two crowns adjacent to each other.

Figure 8:
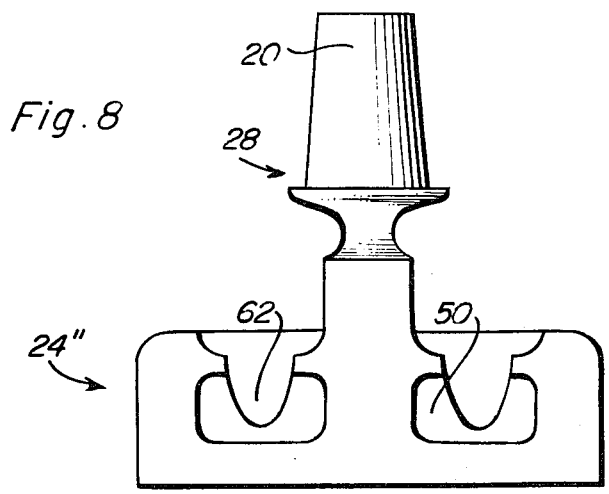
FIG. 8 illustrates yet another form of dental implant constructed in accordance with the present invention.

Whereas, the shank and single abutment support 20 associated with the dental implant 10 shown in FIGS. 1-5, projects from one longitudinal end portion of the base, a similar shank 28 and an abutment support 20 projects centrally from a base 24″ in FIG. 8. Thus, the base 24″ is provided with a pair of stabilizer formations 62 disposed on either side of the shank 28 in FIG. 8 and spaced in overlying relation to associated rectangular openings 50 formed in the base as hereinbefore described with respect to the other embodiments of the invention.

Figure 9:
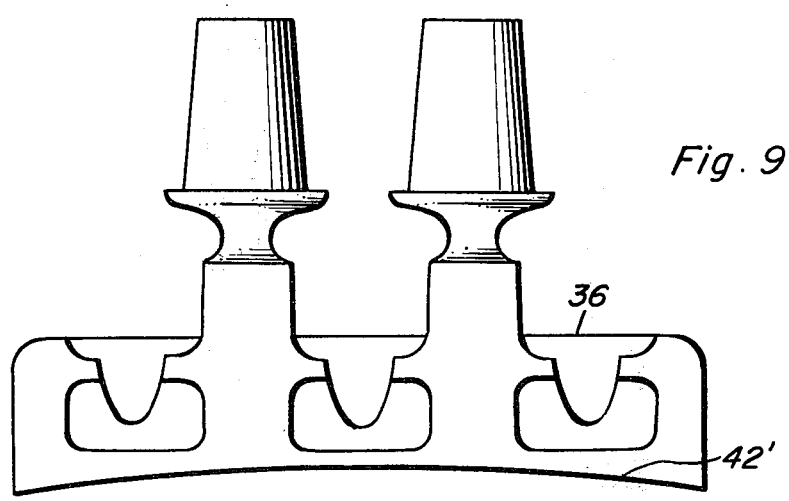
FIG. 9 is a front elevational view of a further form of dental implant constructed in accordance with the present invention.

An implant body for the upper or maxillary jaw is shown in FIG. 9 which is similar to the implant body 10′ shown in FIG. 7 in that a pair of shanks and abutment supports project from the base. However, the two shanks and abutment supports project symmetrically from the base in FIG. 9 as compared to the offset relationship between the shanks and the base shown in FIG. 7. Further, the rounded edge portion 42′ associated with the base in FIG. 9, is not parallel to the flat edge portion 36 as in the other embodiments but extends along a curvature determined by the portion of the maxillae within which the dental implant is embedded.

Figure 10:
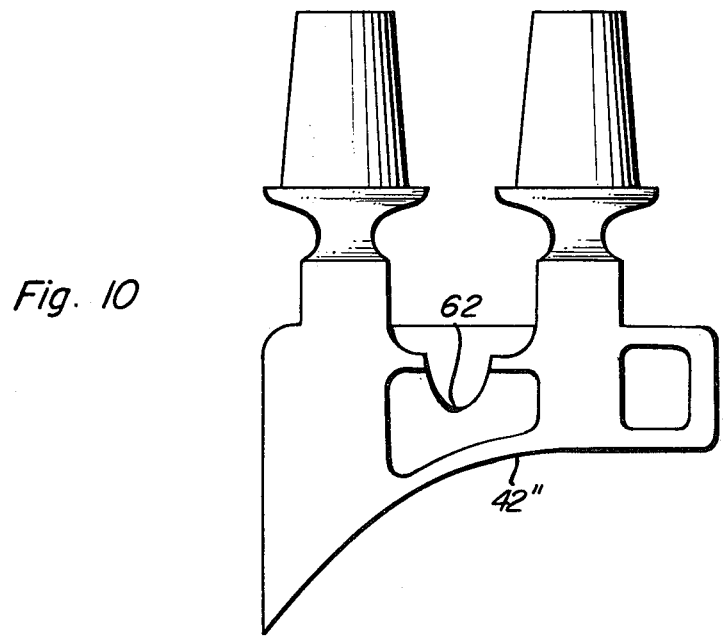
FIG. 10 is a front elevational view of a still further form of dental implant.

In FIG. 10, yet another embodiment of a dental implant for the maxillae is shown wherein a pair of shanks and abutment supports project nonsymmetrically from a base which is provided with an abutment formation 62 and associated opening 50′ between the two shanks. Also, the rounded edge 42″ associated with the base in FIG. 10, is provided with an arcuate curvature.

The various dental implants hereinbefore described are designed for different mandible and maxillae locations and for different types of permanent tooth restorations. Once the type of restoration and location of the dental implant is decided upon, the selected dental implant is embedded in the mandible or maxillae in accordance with approved procedures. Briefly, the implant insertion procedure includes making of a clean incision through the gingival tissue and periosteum in the bony crest. The gingival and periosteum is then retracted after which a recession or trough of the proper width and depth is made in the bone in order to accommodate the implant base and stabilizer. The implant body which has been sterilized is then inserted into the prepared trough with instruments that may be received within the groove 38 or notch 40 as aforementioned. The shoulder portion 52 of the shank will guide the surgeon in finally positioning the implant body with the flat edge 36 of the base spaced 2.5 millimeters from the bony crest. When properly positioned, the abutment support 20 will be properly aligned parallel to the natural abutment teeth in order to insure proper inserting of the finaL bridge. The tissues are then sutured in place about the protruding abutment support 20. After the sutures are removed a permenent crown may be placed over the support and cemented in place.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. In a dental implant for anchoring an artificial tooth in the jawbone of a patient, having a substantially flat base embedded in the bone tissue and at least one substantially non-planar support connected to the base and projecting from the gingival line along a root axis of the tooth, the improvement including a shank extending between said support and the base along said root axis having a neck portion projecting from the ridge crest of the bone tissue toward said gingival line, said neck portion being dimensionally smaller than the base in a cross-sectional plane intersecting the lingual and buccal surfaces of the jawbone, said base including spaced edge portions extending in a mesial-distal direction from the shank transversely of the root axis and an intermediate portion, said intermediate portion being cross-sectionally thinner than the edge portions and having at least one opening formed therein, and a relatively rigid stabilizer connected to and spaced liqually from the base, said stabilizer being connected to one of the edge portions from which the shank projects and aligned with said opening in the base.

2. The dental implant as defined in claim 1 wherein the shank further includes a shoulder portion connecting the neck portion to the base and a gingival collar connecting the neck portion to the support, said neck portion being cross-sectionally smaller than the shoulder portion and the gingival collar, said gingival collar forming a peripheral shoulder surface about the support substantially at the gingival line.

3. The dental implant as defined in claim 2 wherein said shoulder portion of the shank is rectangular in cross-section relative to the root axis and said neck portion is elliptical in cross-section.

4. A dental implant for anchoring an artificial tooth in alignment with a root axis, comprising a blade type of base having spaced edge portions, a shank projecting from one of the edge portions of the base along said root axis and stabilizer means adapted to be embedded with the base entirely within a jawbone and extending only from said one of the edge portions laterally of the base and in offset relation to the shank for resisting turning moments applied to the base, said stabilizer means thereby increasing the spacing of the center of mass of the embedded implant relative to said one of the edge portions.

5. The dental implant as defined in claim 4 wherein said spaced edge portions extend in a mesial-distal direction from the shank transversely of the root axis, the base including an intermediate portion cross-sectionally thinner than the edge portions.

6. A dental implant for anchoring an artifical tooth in alignment with a root axis, comprising a blade type of base having an edge portion, a shank projecting from said edge portion of the base along said root axis, a support connected to the shank on which the artificial tooth is adapted to be seated, and stabilizer means extending laterally from the base and adapted to be embedded therewith entirely within a jawbone for establishing a center of mass enhancing resistance to turning moments applied to the base, said stabilizer means including a rigid element extending only from said edge portion of the base whereby the spacing of the center of mass relative to said edge portion is increased in offset relation to the root axis.

* * * * *